United States Patent
Shalaby et al.

(10) Patent No.: US 6,221,958 B1
(45) Date of Patent: Apr. 24, 2001

(54) IONIC MOLECULAR CONJUGATES OF BIODEGRADABLE POLYESTERS AND BIOACTIVE POLYPEPTIDES

(75) Inventors: Shalaby Wahba Shalaby, Anderson, SC (US); Steven A. Jackson, Holliston; Jacques-Pierre Moreau, Upton, both of MA (US)

(73) Assignees: Societe de Conseils de Recherches et d'Applications Scientifiques, SAS, Paris (FR); Poly-Med Incorporated, Anderson, SC (US)

( * ) Notice: Subject to any disclaimer, the term of this patent is extended or adjusted under 35 U.S.C. 154(b) by 0 days.

(21) Appl. No.: 09/237,405

(22) Filed: Jan. 26, 1999

Related U.S. Application Data

(63) Continuation-in-part of application No. 08/867,308, filed on Jun. 2, 1997, now Pat. No. 5,863,985, which is a continuation of application No. 08/464,735, which is a continuation of application No. PCT/US94/00148, filed on Jan. 5, 1994, now Pat. No. 5,672,659.

(30) Foreign Application Priority Data

Jan. 6, 1993 (IE) .......................................... 930005

(51) Int. Cl.[7] .............................. A61K 9/16; A61K 9/52; A61K 37/02
(52) U.S. Cl. .................... 525/54.1; 514/2; 514/772.3; 514/772.6; 514/800; 514/806; 514/807; 514/808; 514/809
(58) Field of Search .............................. 525/54.1; 514/2, 514/772.3, 772.65, 800, 806, 807, 808, 809

(56) References Cited

U.S. PATENT DOCUMENTS

| | | |
|---|---|---|
| 3,773,919 | 11/1973 | Boswell et al. . |
| 4,356,166 | 10/1982 | Peterson et al. . |
| 4,609,707 | 9/1986 | Nowinski et al. . |
| 4,767,628 | 8/1988 | Hutchinson . |
| 5,071,909 | 12/1991 | Pappin et al. . |
| 5,084,553 | 1/1992 | Hess et al. . |
| 5,162,505 | 11/1992 | Dean et al. . |
| 5,569,467 | 10/1996 | Ruiz . |
| 5,672,659 | 9/1997 | Shalaby et al. . |
| 5,863,985 * | 1/1999 | Shalaby et al. ..................... 525/54.1 |

FOREIGN PATENT DOCUMENTS

| | | |
|---|---|---|
| 0 107 591 A2 | 5/1984 | (EP) . |
| 0 426 055 A3 | 5/1991 | (EP) . |
| 0 467 389 A2 | 1/1992 | (EP) . |
| 0 483 429 A1 | 5/1992 | (EP) . |
| WO 92/11844 | 7/1992 | (WO) . |
| WO 93/17668 | 9/1993 | (WO) . |
| WO 94/15587 | 7/1994 | (WO) . |

OTHER PUBLICATIONS

Mehta, R.C. et al., "Biodegradable Microspheres as Depot System for Parenteral Delivery of Peptide Drugs", J of Controlled Release, 29 (1994) 375–384.

Shah et al., "Poly (glycolic acid co–DL–lactic acid); Diffusion or Degradation Controlled Drug Delivery?", J. of Controlled Realeas, 18:261–270, 1992.

* cited by examiner

Primary Examiner—Nathan M. Nutter
(74) Attorney, Agent, or Firm—John D. Conway; Brian R. Morrill; Fish & Richardson

(57) ABSTRACT

Disclosed is a sustained release pharmaceutical composition. The composition includes a polyester containing a free COOH group ionically conjugated with a bioactive polypeptide comprising at least one effective ionogenic amine, wherein at least 50% by weight of the polypeptide present in the composition is ionically conjugated to the polyester.

42 Claims, 3 Drawing Sheets

Forms of Lactate / Glycolate - Type Polymers of Polycarboxylic Acid-Tipped Chains

LINEAR CHAINS

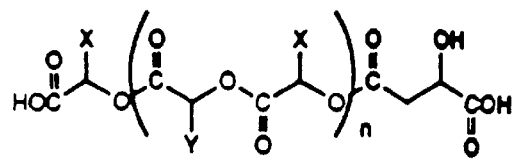

Di End Acid-Terminal Malic

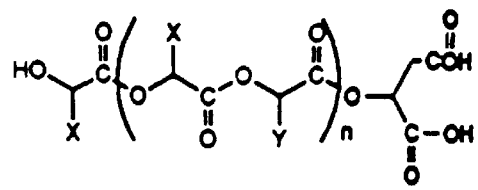

End Hydroxy-Terminal Malic

BRANCHED CHAINS

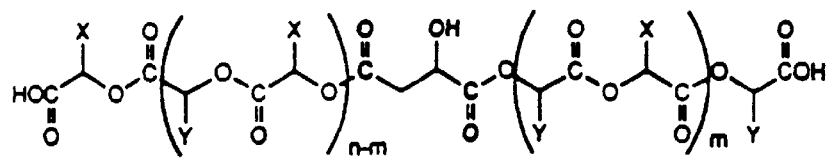

Di End Acid-Internal Malic

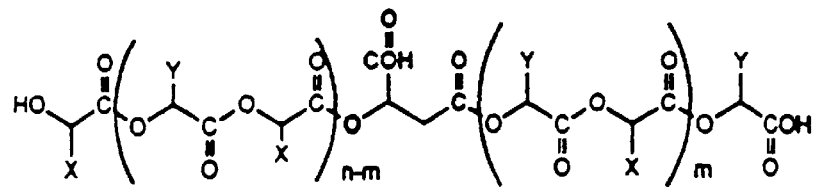

End Hydroxy-Internal Malic

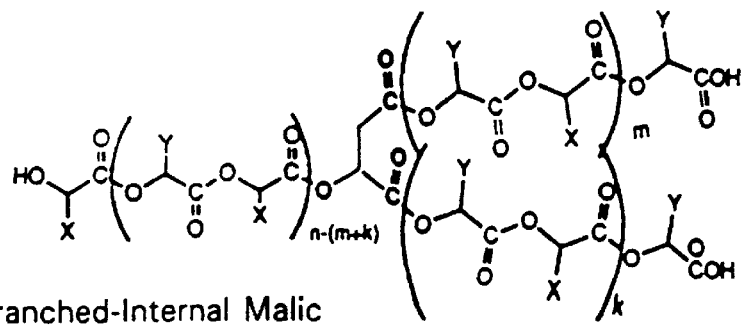

Fully Branched-Internal Malic

Y = CH$_3$ for Lactic, H for Glycolic; X = H for Glycolic, CH$_3$ for Lactic
Distribution of X + Y is formula dependent and polymerization dependent

FIG. 1

IONIC MOLECULAR CONJUGATES OF BIODEGRADABLE POLYESTERS AND BIOACTIVE POLYPEPTIDES

CROSS REFERENCE TO RELATED APPLICATIONS

This application is a continuation-in-part of application Ser. No. 08/867,308, filed Jun. 2, 1997, which will issue as U.S. Pat. No. 5,863,985 on Jan. 26, 1999, which is a continuation application of application Ser. No. 08/464,735, filed Jun. 29, 1995, now issued as U.S. Pat. No. 5,672,659 on Sep. 30, 1997, which is a continuation of PCT/US94/00148, filed Jan. 5, 1994, which is a PCT Phase application of Irish Application No. 930005 filed Jan. 6, 1993.

BACKGROUND OF THE INVENTION

This invention pertains to sustained release of bioactive polypeptides.

Many drug delivery systems have been developed, tested and utilized for the controlled in vivo release of pharmaceutical compositions. For example, polyesters such as poly (DL-lactic acid), poly (glycolic acid), poly ($\epsilon$-caprolactone) and various other copolymers have been used to release biologically active molecules such as progesterone; these have been in the form of microcapsules, films, or rods (Pitt C G, Marks, T A, and Schindler, A. 1980). Upon implantation of the polymer/therapeutic agent composition, for example subcutaneously or intramuscularly, the therapeutic agent is released over a specific period of time. Such biocompatible biodegradable polymeric systems are designed to permit the entrapped therapeutic agent to diffuse from the polymer matrix. Upon release of the therapeutic agent, the polymer is degraded in vivo, obviating surgical removal of the implant. Although the factors that contribute to polymer degradation are not well understood, it is believed that such degradation for polyesters may be regulated by the accessibility of ester linkages to non-enzymatic autocatalytic hydrolysis of the polymeric components.

Several EPO publications and U.S. patents have addressed issues of polymer matrix design and its role in regulating the rate and extent of release of therapeutic agents in vivo.

For example, Deluca (EPO Publication 0 467 389 A2/Univ of Kentucky) describes a physical interaction between a hydrophobic biodegradable polymer and a protein or polypeptide. The composition formed was a mixture of a therapeutic agent and a hydrophobic polymer that sustained its diffusional release from the matrix after introduction into a subject.

Hutchinson (U.S. Pat. No. 4,767,628/ICI) controlled the release of a therapeutic agent by uniform dispersion in a polymeric device. It is stated that this formulation provides for controlled continuous release by the overlap of two phases: first, a diffusion-dependent leaching of the drug from the surface of the formulation; and second, releasing by aqueous channels induced by degradation of the polymer.

SUMMARY OF THE INVENTION

In general, the invention features a sustained release pharmaceutical formulation composed of a polyester containing free COOH groups ionically conjugated with a biologically active polypeptide composed of at least one effective, ionogenic amine wherein at least 50%, by weight, of the polypeptide present in the composition is ionically conjugated to the polyester.

In preferred embodiments, the polyester is modified to increase the carboxyl to hydroxyl end group ratio from more than one and approaches infinity, i.e., all of the hydroxyl groups can be substituted with carboxyls. Examples of suitable polyesters are those originating from compounds such as L-lactic acid, D-lactic acid, DL-lactic acid, $\epsilon$-caprolactone, p-dioxanone, $\epsilon$-caproic acid, substituted and unsubstituted trimethylene carbonate (TMC), 1,5-dioxepan-2-one, 1,4-dioxepan-2-one, glycolide, glycolic acid, L-lactide, D-lactide, DL-lactide, meso-lactide, alkylene oxalate, cycloalkylene oxalate, alkylene succinate, ($\beta$-hydroxybutyrate), and optically active isomers, racemates or copolymers of any of the above, wherein the substituted TMC is substituted with ($C_1$–$C_4$)alkyl, preferably methyl. Other heterochain polymers related to traditional polyesters may also be used (e.g., polyorthoesters, polyorthocarbonates, and polyacetals).

Preferably, the polyester is made polycarboxylic by reaction with malic acid, citric acid or tartaric acid.

In preferred embodiments the polyester is partially acid-tipped with glutaric anhydride. In yet other preferred embodiments the polyester is fully acid-tipped with glutaric anhydride. Preferably, the polyester has an average degree of polymerization between 10 and 300 and more preferably between 20 to 50.

The ionic molecular conjugates of the invention are preferably made from polycarboxylic acid-tipped polyesters conjugated with monobasic and polybasic bioactive polypeptides having at least one effective ionogenic amine group. Alternatively, any polyester may be used to form an ionic molecular conjugate of the invention provided it is pretreated with a suitable base, e.g., NaOH. Moreover, any acid-stable peptide can be used, e.g., growth hormone releasing peptide (GHRP), luteinizing hormone-releasing hormone (LHRH), somatostatin, bombesin, gastrin releasing peptide (GRP), calcitonin, bradykinin, galanin, melanocyte stimulating hormone (MSH), growth hormone releasing factor (GRF), amylin, tachykinins, secretin, parathyroid hormone (PTH), enkephalin, endothelin, calcitonin gene releasing peptide (CGRP), neuromedins, parathyroid hormone related protein (PTHrP), glucagon, neurotensin, adrenocorticotrophic hormone (ACTH), peptide YY (PYY), glucagon releasing peptide (GLP), vasoactive intestinal peptide (VIP), pituitary adenylate cyclase activating peptide (PACAP), motilin, substance P, neuropeptide Y (NPY), TSH, and analogs and fragments thereof. Such ionic molecular conjugates are capable of releasing their bioactive components in vivo at predetermined rates determined by the chemical structure, molecular weight, and pKa of both components of these conjugates. A mechanism for the release of the drug entails the transformation of the insoluble conjugate form to water-soluble components, in part, through the hydrolysis of the hydrophobic polyester. Thus, release of the bioactive polypeptide increases, independently, with (a) the decrease in the pKa differential between the bioactive polypeptide and polyester, (b) the chemical reactivity of the polyester chain that is reflected in the carbonyl nucleophilicity, (c) the decrease in polyester density, as it relates to the glass transition temperature and minimized crystallizability, and (d) the increase in matrix hydrophilicity.

In preferred embodiments the polypeptide comprises 1 to 50 percent by weight of the total weight of the ionic molecular conjugate, and preferably greater than 85%, more preferably 95%, and even more preferably 99%, of the polypeptide present in the composition is ionically conjugated to the polyester; the polyester component of the ionic molecular conjugate has a viscosity of about 0.05 to about 0.7 dl/gm in chloroform; and the polyester has an average molecular weight of about 1200–40,000.

The polymeric ionic molecular conjugates of the invention can easily be made into injectable microspheres or microparticles, and implantable films or rods, without the need to utilize processing that entails multiphase emulsions or non-aqueous two-phase systems. Preferably, the microparticles are manufactured by (a) dissolving the composition in an aprotic, water miscible organic solvent; (b) mixing the organic solvent in water; and (c) isolating the microparticles from the water. In preferred embodiments, the organic solvent is chosen from the group of acetone, acetonitrile, tetrahydrofuran, dimethylformamide, and dimethoxy ethylene glycol.

In preferred embodiments the polyester/polypeptide ionic molecular conjugate is capable of releasing in vivo a therapeutically effective dose of a bioactive polypeptide over a period of at least 20 days, and more preferably for up to 95 days but not less than 7 days. In yet other preferred embodiments the release of the therapeutic ionic molecular conjugate is essentially monophasic.

The sustained release compositions of the invention are preferably made by (a) providing a polyester having free COOH groups and a bioactive polypeptide having at least one effective ionogenic amine, and (b) ionically conjugating the polyester to the polypeptide to form an ionic molecular conjugate, wherein at least 85%, by weight, of the polypeptide present in the composition is ionically conjugated to the polyester. The polyester can be one which has sufficient free COOH groups to begin with, or, if an insufficient number of such groups are available for the desired peptide loading level at the outset, the polyester can be (1) reacted with, e.g., malic, citric or tartaric acid through esterification or functional interchange, or (2) acid-tipped with, e.g., glutaric anhydride or (3) the polyester can be treated with a base, e.g., NaOH, to expose acid groups. Finally, the polyester/polypeptide ionic molecular conjugate may be converted to implantable films or rods, or injectable microspheres or microparticles capable of releasing in vivo the polypeptide.

Preferably, the polyester is synthesized by catalyzing or autocatalyzing direct condensation of one or more hydroxy acids, e.g., glycolic acid and lactic acid, in the presence of a predetermined concentration of a polycarboxylic hydroxy acid, e.g., malic acid, citric acid or tartaric acid. The polyesters thus formed possess acid-tipped hydroxyl end groups which are preferably partially or fully acid-tipped.

The polyesters also can be synthesized by catalyzing ring-opening polymerization of lactones, or by polymerization of cyclic monomers such as $_\epsilon$-caprolactone, p-dioxanone, trimethylene carbonate, 1,5-dioxepan-2-one, or, 1,4-dioxepan-2-one in the presence of a chain initiator, e.g., a hydroxy polycarboxylic acid.

Another method of synthesizing involves reacting a hydroxy acid with a cyclic dimer, followed by condensation of the open chain system in the presence of a polycarboxylic acid.

Yet another synthetic method involves reacting an organic polycarboxylic acid with a preformed polyester.

In the aforementioned preferred embodiments the acid-Upped polyester has a carboxyl to hydroxyl end group ratio of more than one and approaching infinity (i.e, eliminating all the hydroxyl groups) with an average degree of polymerization between 10 and 300, and in particularly preferred embodiments between 20 and 50.

Alternatively, a polyester is rendered capable of forming an ionic molecular conjugate with a bioactive polypeptide by treatment with a base, e.g, NaOH.

Preferably, the polyester/polypeptide ionic molecular conjugate is synthesized by direct interaction between the polyester, e.g., in the free form, and the polypeptide, e.g., in the free form, in the proper liquid medium. In other preferred embodiments suitable solvents for the formation of the conjugate would be a mixture aprotic solvent [e.g., acetone, tetrahydrofuran (THF), or ethylene glycol dimethylether] and a suitable solvent for the peptide (e.g., water) in proportions such that the two systems are miscible. Preferably, the polypeptide is a salt of a monocarboxylic acid having a pKa greater than or equal to 3.5. Preferably, the polypeptide has at least one effective ionogenic amine group.

In preferred embodiments the polypeptide is 1 to 50 percent by weight, and preferably 10 to 20 percent of the polyester/polypeptide ionic molecular conjugate. In preferred embodiments, the accessible carboxyl groups of the polyester are partially neutralized with alkali metal ions or organic bases. In yet other preferred embodiments, the alkali treatment provides chain dissociation of the polyester and formation of lower molecular weight binding sites.

In another aspect, the present invention is directed to a polyester (designated polyester A) containing one or more free COOH groups and having a carboxyl to hydroxyl ratio greater than one, wherein said polyester contains a member selected from the group consisting of L-lactic acid, D-lactic acid, DL-lactic acid, malic acid, citric acid, $_\epsilon$-caprolactone, p-dioxanone, $_\epsilon$-caproic acid, alkylene oxalate, cycloalkylene oxalate, alkylene succinate, β-hydroxybutyrate, substituted or unsubstituted trimethylene carbonate, 1,5-dioxepan-2-one, 1,4-dioxepan-2-one, glycolide, glycolic acid, L-lactide, D-lactide, DL-lactide, meso-lactide, and any optically active isomers, racemates or copolymers thereof, provided that citric acid, $_\epsilon$-caprolactone and glycolide are members of the polyester. A preferred embodiment of the foregoing polyester (designated polyester B) is where the polyester comprises citric acid, $_\epsilon$-caprolactone and glycolide. A preferred embodiment of the immediately foregoing polyester (designated polyester C) is where the ratio of $_\epsilon$-caprolactone to glycolide in the polyester is from 90 $_\epsilon$-caprolactone:10 glycolide to 99 $_\epsilon$-caprolactone:1 glycolide. A preferred polyester of the immediately foregoing polyester (designated polyester D) is where the ratio of $_\epsilon$-caprolactone to glycolide in the polyester is 97 $_\epsilon$-caprolactone:3 glycolide.

In yet another aspect, the present invention is directed to a composition comprising polyester A, polyester B, polyester C or polyester D, ionically conjugated to one or more bioactive polypeptide comprising at least one effective ionogenic amine, wherein at least 50%, by weight, of the polypeptide present in the composition is ionically conjugated to the polyester.

A preferred embodiment of the immediately foregoing composition is where the bioactive polypeptide is selected from the group consisting of LHRH, somatostatin, bombesin/GRP, calcitonin, bradykinin, galanin, MSH, GRF, amylin, tachykinins, secretin, PTH, CGRP, neuromedins, PTHrP, glucagon, neurotensin, ACTH, GHRP, GLP, VIP, PACAP, enkephalin, PYY, motilin, substance P, NPY, TSH, and analogs or fragments thereof.

A preferred embodiment of the immediately foregoing composition is where the bioactive polypeptide is selected from the group consisting of LHRH, somatostatin and analogs or fragments thereof.

A preferred embodiment of the immediately foregoing composition is where the LHRH analogue is of the formula pGlu-His-Trp-Ser-Tyr-D-Trp-Leu-Arg-Pro-Gly-NH$_2$ and the somatostatin analogue is of the formula H$_2$N-β-D-Nal- Cys-Tyr-Trp-Lys-Val-Cys-Thr-NH$_2$, wherein the two Cys residues of the somatostatin analogue are bonded to each other.

A preferred embodiment of the immediately foregoing composition is where the composition is in the form of a rod.

A preferred embodiment of the immediately foregoing composition is where the rod has a coating of a polyester.

A preferred embodiment of the immediately foregoing composition is where the polyester coating the rod is an absorbable polyester.

A preferred embodiment of the immediately foregoing composition is where the absorbable polyester contains one or more free COOH groups and having a carboxyl to hydroxyl ratio greater than one, wherein said polyester contains a member selected from the group consisting of L-lactic acid, D-lactic acid, DL-lactic acid, malic acid, citric acid, tartaric acid, $_\epsilon$-caprolactone, p-dioxanone, $_\epsilon$-caproic acid, alkylene oxalate, cycloalkylene oxalate, alkylene succinate, β-hydroxybutyrate, substituted or unsubstituted trimethylene carbonate, 1,5-dioxepan-2-one, 1,4-dioxepan-2-one, glycolide, glycolic acid, L-lactide, D-lactide, DL-lactide, meso-lactide, and any optically active isomers, racemates or copolymers thereof.

A preferred embodiment of the immediately foregoing composition is where the absorbable polyester coating the rod is the same as the polyester comprised in the composition.

In still another aspect, the present invention is directed to a polyester (designated polyester E) containing one or more free COOH groups and having a carboxyl to hydroxyl ratio greater than one, wherein said polyester contains a member selected from the group consisting of L-lactic acid, D-lactic acid, DL-lactic acid, malic acid, citric acid, tartaric acid, $_\epsilon$-caprolactone, p-dioxanone, $_\epsilon$-caproic acid, alkylene oxalate, cycloalkylene oxalate, alkylene succinate, β-hydroxybutyrate, substituted or unsubstituted trimethylene carbonate, 1,5-dioxepan-2-one, 1,4-dioxepan-2-one, glycolide, glycolic acid, L-lactide, D-lactide, DL-lactide, meso-lactide, and any optically active isomers, racemates or copolymers thereof, provided that tartaric acid is a member of the polyester. A preferred embodiment of the foregoing polyester (designated polyester F) is where the polyester comprises L-lactic acid or D-lactic acid; or wherein the polyester comprises L-lactic acid or D-lactic acid and glycolic acid. Another preferred embodiment of polyester E (designated polyester G) is where the polyester comprises tartaric acid, $_\epsilon$-caprolactone and trimethylene carbonate. A preferred embodiment of the immediately foregoing polyester (designated polyester H) is where the ratio of $_\epsilon$-caprolactone to trimethylene carbonate in the polyester is from 90 $_\epsilon$-caprolactone:10 trimethylene carbonate to 99 $_\epsilon$-caprolactone:1 trimethylene carbonate. A preferred embodiment of the immediately foregoing polyester (designated polyester I) is where the ratio of $_\epsilon$-caprolactone to trimethylene carbonate in the polyester is 98 $_\epsilon$-caprolactone:2 trimethylene carbonate.

In still yet another aspect, the present invention is directed to a composition comprising polyester E, polyester F, polyester G, polyester H or polyester I, ionically conjugated to one or more bioactive polypeptide comprising at least one effective ionogenic amine, wherein at least 50%, by weight, of the polypeptide present in the composition is ionically conjugated to the polyester.

A preferred embodiment of the immediately foregoing composition is where the bioactive polypeptide is selected from the group consisting of LHRH, somatostatin, bombesin/GRP, calcitonin, bradykinin, galanin, MSH, GRF, amylin, tachykinins, secretin, PTH, CGRP, neuromedins, PTHrP, glucagon, neurotensin, ACTH, GHRP, GLP, VIP, PACAP, enkephalin, PYY, motilin, substance P, NPY, TSH, and analogs or fragments thereof.

A preferred embodiment of the immediately foregoing composition is where the bioactive polypeptide is selected from the group consisting of LHRH, somatostatin and analogs or fragments thereof.

A preferred embodiment of the immediately foregoing composition is where the LHRH analogue is of the formula pGlu-His-Trp-Ser-Tyr-Trp-Leu-Arg-Pro-Gly-NH$_2$ and the somatostatin analogue is of the formula H$_2$N-β-D-Nal-Cys-Tyr-Trp-Lys-Val-Cys-Thr-NH$_2$, wherein the two Cys residues of the somatostatin analogue are bonded to each other.

A preferred embodiment of the immediately foregoing composition is where the composition is in the form of a rod.

A preferred embodiment of the immediately foregoing composition is where the rod has a coating of a polyester.

A preferred embodiment of the immediately foregoing composition is where the absorbable polyester contains one or more free COOH groups and having a carboxyl to hydroxyl ratio greater than one, wherein said polyester contains a member selected from the group consisting of L-lactic acid, D-lactic acid, DL-lactic acid, malic acid, citric acid, tartaric acid, $_\epsilon$-caprolactone, p-dioxanone, $_\epsilon$-caproic acid, alkylene oxalate, cycloalkylene oxalate, alkylene succinate, β-hydroxybutyrate, substituted or unsubstituted trimethylene carbonate, 1,5-dioxepan-2-one, 1,4-dioxepan-2-one, glycolide, glycolic acid, L-lactide, D-lactide, DL-lactide, meso-lactide, and any optically active isomers, racemates or copolymers thereof.

A preferred embodiment of the immediately foregoing composition is where the absorbable polyester coating the rod is the same as the polyester comprised in the composition.

"Polypeptide", as used herein, refers to a protein, peptide, oligopeptide or synthetic oligopeptide.

"Polycarboxylic", as used herein, refers to compounds having more than one carboxyl group, e.g., malic acid, citric acid and tartaric acid.

"Average degree of polymerization", as used herein, refers to the number of repeat monomer sequences.

"Effective ionogenic amine", as used herein, refers to a polypeptide that contains at least one amine group capable of forming an ion under prevailing conditions.

"Acid-tipped", as used herein, refers to compounds having an acid terminus.

"Partially acid-tipped", as used herein, refers to compounds having 1–99 percent of their hydroxyl end groups acid-tipped.

"Fully acid-tipped", as used herein, refers to compounds having greater than 99.9% of their hydroxyl groups acid-tipped.

"Hydroxy acids", as used herein, refers to any compound containing hydroxyl and carboxyl groups.

"Monocarboxylic hydroxy acid", as used herein, refers to an organic acid with one carboxyl group and one or more hydroxyl group.

"Polycarboxylic hydroxy acid", as used herein, refers to a hydroxy acid with more is than one carboxyl group.

"Organic entrainer", as used herein, refers to organic liquids which codistill with water.

"Bioactive", as used herein, refers to a molecule that elicits or affects a biological event.

"Acyclize", as used herein, refers to a chemical reaction that occurs by ring opening.

"Polycondensation", as used herein, refers to the formation of a polyester by the condensation of two or more molecules.

"Absorbable" polyester, as used herein, refers to a water insoluble polyester which undergoes chain disassociation in the biological environment to water soluble by-products.

The present invention provides a new pharmaceutical composition that chemically bonds a biocompatible, biodegradable polyester to oligopeptides, polypeptides, peptides and or proteins as a homogeneous ionic species. By chemically bonding polyesters of different molecular weights to the therapeutic agents, the chemical characteristics of the composition can be more precisely tailored to meet the demands for the controlled monophasic release of the biologically active polypeptide molecule in vivo. Furthermore, the compositions of the invention are optimized easily to possess functional properties for greater loading of a therapeutically active polypeptide.

Other features and advantages of the invention will be apparent from the following detailed description of the preferred embodiments, and from the claims.

BRIEF DESCRIPTION OF THE DRAWINGS

FIG. 1 is an illustration representing isomers of polycarboxylic acid-tipped lactide/glycolide (malic type) copolymer.

DESCRIPTION OF THE PREFERRED EMBODIMENTS

Synthesis

Figure 2:
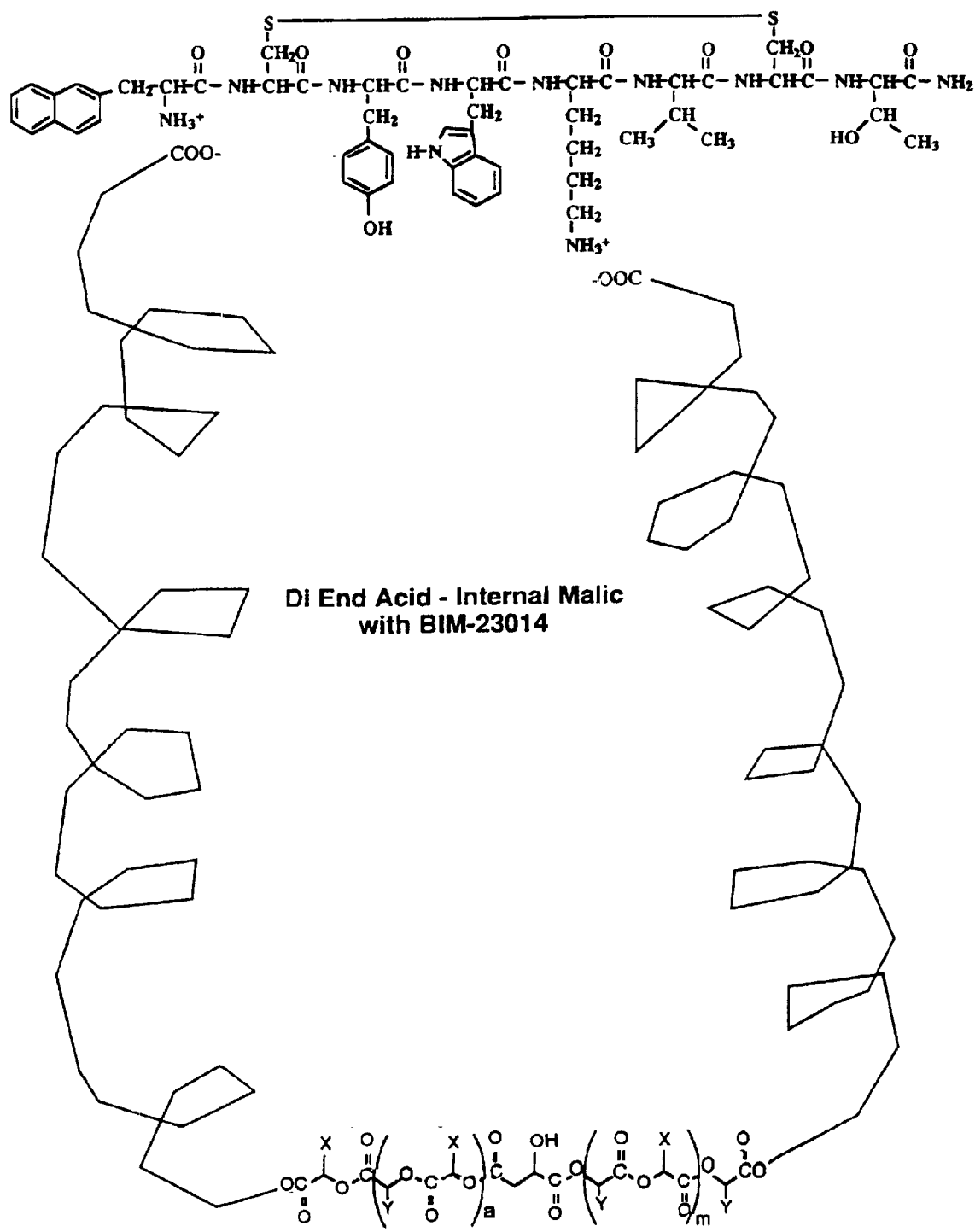
FIG. 2 is an illustration of an ionic molecular conjugate depicting the chemical interactions between the lactide/glycolide (malic type) copolymer and Somatuline (BIM-23014).
Figure 3:
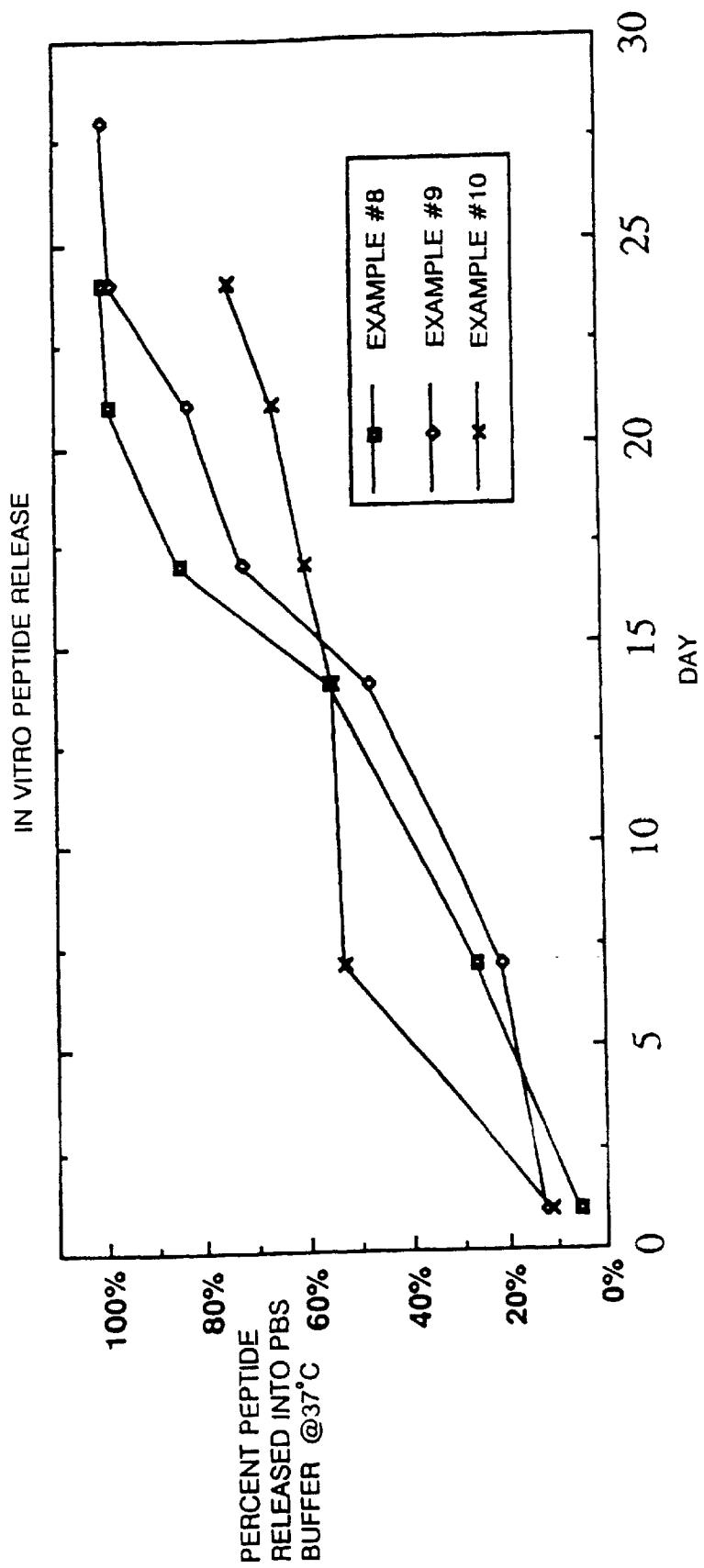
FIG. 3 is a graph depicting the percent peptide released from ionic molecular conjugates into PBS buffer at 37° C. over a 28-day period.

The biodegradable or absorbable polyesters of the invention are tailored to possess the desired chemical reactivity to provide controlled chain hydrolyzability and exhibit maximum binding capacity to oligopeptides, polypeptides or proteins having a net positive charge at physiologic pH, by the proper selection of the constituent monomers, co-monomers or comers to form chains with predetermined compositions and molecular weights.

A tripartite synthetic design, within the ability of someone of ordinary skill in this field, is employed to prepare the compositions of the present invention. The steps include: (1) synthesis of the polycarboxylic acid-tipped polyesters; (2) synthesis of the polyester/polypeptide ionic conjugate by ionic interaction of polycarboxylic acid-tipped polyesters (or a polyester treated with a base) and biologically active polypeptides; and (3) conversion of ionic conjugates to implants, rods, microspheres or microparticles capable of releasing in vivo the therapeutic agent for at least 7 days.

(1) Synthesis of polycarboxylic acid-tipped polyesters

The polycarboxylic acid-tipped polyester chains of the invention are synthesized by methods such as direct condensation of a 2-hydroxy acid and a polycarboxylic organic acid, step-growth polymerization of acyclized products, ring-opening polymerization of a lactone or a lactone mixture, or functional interchange of a polycarboxylic organic acid with preformed high molecular weight polyesters (See FIG. 1) Descriptions of the synthesis of polycarboxylic acid-tipped polyesters by these aforementioned methods follow.

Direct condensation of 2-hydroxy acids in an optically active and/or an inactive form and a predetermined amount of a polycarboxylic organic acid in the presence or absence of inorganic, or organometallic catalyst, e.g., condensation of glycolic acid DL-lactic acid, and DL-malic acid is generally accomplished by heating the monocarboxylic hydroxy acids or mixture of two or more monocarboxylic hydroxy acid in the presence of a fraction of polycarboxylic hydroxy acid in a glass reactor equipped for providing a continuous flow of dry-nitrogen and mass agitation (designated Type IA Polyester, see Table I). Typically, the polycondensation is conducted at 150–170° C. for 4 to 72 hours. Agitation of the reaction mixture can be provided by a magnetic stirrer or bubbling the nitrogen gas through the polyester mass. The polymerization is continued until the desired average molecular weight (determined in terms of solution viscosity) and/or acid number (determined by end group titration) is achieved. Polyester analysis by end group titration is performed as follows. Polyester samples (300 mg–500 mg) are accurately weighed and dissolved in a minimal amount (10–30 ml) of acetone. After dissolution, the solutions are diluted to 100 ml with benzyl alcohol (Mallinckrodt, Analytical Reagent) and titrated to a faint pink end-point (phenolphthalein) using potassium hydroxide in benzyl alcohol solution (Normalized vs. HCl Standard). The volume of base solution used for the sample ($_A$Vs) is compared with the volume of base used for a solvent blank ($_A$Vo) to determine the acid number for the polyester.

$$\text{Acid \#} = \frac{\text{Wt. of Sample (mg)}}{\{\Delta Vs(\text{ml}) - \Delta Vo(\text{ml})\} \times N \text{ of Base}}$$

At the conclusion of polymerization, the polyester is isolated and extracted with water or a dilute aqueous sodium hydroxide solution, from a suitable organic solution to remove water-soluble or solubilizable low molecular weight chains.

Polyester analysis by GPC is performed as follows. The average molecular weights (MW) of polyester were determined by GPC using a Waters Model 6000 solvent delivery pump and a Dynamax (Rainin) model UV-D detector. Runs were performed in tetrahydrofuran (Burdick & Jackson UV grade) using a Jordi Gel DVB 1000 Å, 50 cm×10 mm column (Jordi Associates) at a flow rate of 1.2 ml/min at 25 C. Peak detection was at 220 nm and 1.0 AUFS. The column was calibrated using narrow band polystyrene reference standards (Polysciences Inc.) at Mw=4000, 9,200 and 25,000.

A modification of the direct condensation process entails the use of an organic entrainer and a cationic exchange resin as a condensation catalyst (designated Type IB Polyester, see Table I). This process requires a filtration and evaporation step to remove the catalyst and entrainer, respectively. Typical examples of polyesters made by these processes and pertinent analytical data are described in Table I.

TABLE I

POLYESTERS MADE BY DIRECT CONDENSATION METHOD

| Polymer # | | Charge | Polymerization Conditions | Acid # | ηinh | Tg, °C. |
|---|---|---|---|---|---|---|
| Type IA Polyesters | | | | | | |
| 1 | L-Lactic Acid (88%) | 35.7 gm (0.349 M) | 100° C./0.7 hr | 563 | 0.24 | 11 |
|   | Glycolic Acid | 4.65 gm (0.612 M) | 165° C./17.5 hrs | | | |
|   | Citric Acid | 1.75 gm (0.0091 M) | | | | |
| 2 | L-Lactic Acid (88%) | 25.6 gm (0.25 M) | 165° C./22 hrs | 820 | 0.14 | 27 |
|   | Glycolic Acid | 19.2 gm (0.25 M) | | | | |
|   | Malic Acid | 1.5 gm (0.011 M) | | | | |
| Type IB Polyesters | | | | | | |
| 3 | L-Lactic Acid (88%) | 25.6 gm (0.25 M) | 132° C./53 hrs | 842 | 0.11 | 15 |
|   | Glycolic Acid | 19.2 gm (0.25 M) | | | | |
|   | Citric Acid | 2.13 gm (0.011 M) | Using Dean-Stark Trap. Decanted, filtered in Acetone. Dried. Washed with water. Vacuum dried. | | | |
|   | Amberlyst Catalyst Beads #15 | 0.5 gm | | | | |
|   | Toluene | 150 ml | | | | |
| 4 | L-Lactic Acid (88%) | 25.6 gm (0.25 M) | 132 ° C./68 hrs | 1421 | 0.20 | 28 |
|   | Gycolic Acid | 19.2 gm (0.25 M) | | | | |
|   | Malic Acid | 1.5 gm (0.011 M) | Using Dean-Stark Trap. Decanted, Filtered, Dried. Washed with water and Vacuum Dried. | | | |
|   | Amberlyst | | | | | |
|   | Toluene | 100 ml | | | | |

*Determined on a differential scanning calorimeter (TA 2100 DSC) using 2–10 mg sample and heating rate of 10° C./min in a nitrogen atmosphere Step-growth polymerization of acyclized products, where a hydroxy acid is allowed to react with cyclic dimers and subsequent condensation of the resulting open chain system in the presence of predetermined amounts of a polycarboxylic acid and the presence or absence of a suitable condensation catalyst e.g. glycolic acid, L-lactide and DL-malic acid, essentially the same as the condensation process described above, except that it employs a mixture of a monocarboxylic hydroxy-acid, a cyclic dimer of a second hydroxy-acid, and a hydroxy polycarboxylic acid. Examples of polyesters made by this process and pertinent analytical data are summarized in Table II. When the cyclic dimer is pretreated with water the system is treated as a simple step-growth polymerization.

Ring opening polymerization of a lactone or lactone mixture in the presence of a predetermined concentration of hydroxy-polycarboxylic acid as a chain initiator and a catalytic amount of an organometallic catalyst e.g. a mixture of L-lactide, glycolide and DL-malic acid in the presence of stannous octoate employs dry cyclic monomers or a mixture of cyclic monomers, a hydroxy-polycarboxylic acid and a trace amount of stannous octoate (used as 0.33M solution in toluene), which are transferred under a dry oxygen-free atmosphere into a glass reactor equipped for magnetic or mechanical stirring. The polymerization reaction is continued under nitrogen following a suitable heating scheme until the desired molecular weight is achieved (as measured in terms of solution viscosity). At the conclusion of the poly

TABLE II

STEP-GROWTH POLYMERIZATION OF ACYCLIZED PRODUCTS

| Polymer # | | Charge | Polymerization Conditions | Acid # | ηinh | Tg, °C. |
|---|---|---|---|---|---|---|
| Type II Polyesters | | | | | | |
| 1 | L-Lactide Monomer | 10.0 gm (0.07 M) | 160° C./29 hrs | 1200 | 0.21 | 20 |
|   | Glycolic Acid | 10.7 gm (0.14 M) | | | | |
|   | Malic Acid | 0.79 gm (0.0061 M) | | | | |
| 2 | L-Lactide Monomer | 20.0 gm (0.139 M) | 25° C.–155° C./1.5 h | 1800 | 0.13 | 27 |
|   | Glycolic Acid | 7.1 gm (0.093 M) | 155° C./70 hr | | | |
|   | Malic Acid | 1.01 gm (0.0075 M) | Dissolve in DCM wash with water, and dry in vacuo. | | | |

*Determined on a differential scanning calorimeter (TA2100 DSC) using 2–10 mg sample and heating rate of 10° C./min in a nitrogen atmosphere merization scheme, the temperature is lowered and the unreacted monomer is distilled under reduced pressure. The polyester mass is then cooled and the water-soluble low molecular weight fractions are removed by low temperature extraction from a suitable organic solution. The solution is then dried and the solvent is removed. The molecular weight is then determined in terms of inherent viscosity and the acid number is determined by end-group titration. Examples of polyesters prepared by this process and pertinent analytical data are given in Table III.

nitrogen with intensive agitation until the functional interchange is completed (as measured by depletion of residual unreacted polycarboxylic acid). In effect this is determined by monitoring the molecular weight (in terms of solution viscosity using capillary viscometry at 28° C.) of the resultant lower molecular weight polyester and the presence of unreacted polycarboxylic acid. This is achieved by aqueous extraction of a polyester sample and analysis of the extract using high performance liquid chromatography (HPLC). Residual monomer, dimer and polycarboxylic acid levels

TABLE III

POLYESTERS MADE BY RING OPENING POLYMERIZATION

Type III Polyesters

| Polymer # | Charge | | Polymerization Conditions | Acid # | $\eta$inh | Tg, ° C.* |
|---|---|---|---|---|---|---|
| 1 | Glycolide | 3.22 gm (0.028 M) | 120° C./0.5 hr | 2,150 | 0.79** | 38 |
|   | L-Lactide | 10.7 gm (0.14 M) | 150° C./6 hrs |  |  |  |
|   | Malic Acid | 0.79 gm (0.0061 M) | 120° C./11 hrs |  |  |  |
| 2 | Glycolide | 2.84 gm (0.0245 M) | 120° C./0.5 hr | 1,206 | 0.08 | 26 |
|   | D,L-Lactide | 20.0 gm (0.139M) | 180° C./2.5 hrs |  |  |  |
|   | Malic Acid | 0.876 gm (0.00541 M) | 130° C./15 hrs |  |  |  |
| 3 | Glycolide | 2.84 gm (0.0245 M) | 155° C./1 hr | 937 | 0.10 | 27 |
|   | D,L-Lactide | 20.0 gm (0.139 M) | 185° C./2.5 hrs |  |  |  |
|   | Citric Acid | 1.256 gm (0.00654 M) | 190° C./2.5 hrs |  |  |  |
|   |  |  | 160° C./13 hrs |  |  |  |
| 4 | Glycolide | 8.06 gm (0.0694 M) | 180° C./1 hr | 970 | 0.26 | 23 |
|   | D,L-Lactide | 10.0 gm (0.0694 M) | 185° C./2 hrs |  |  |  |
|   | Malic Acid | 0.744 gm (0.00555 M) | 195° C./7 hrs |  |  |  |
|   |  |  | 120° C./9 hrs |  |  |  |
| 5 | Glycolide | 8.06 gm (0.0694 M) | 150° C./0.5 hr | 10,138 | 0.39 | 30 |
|   | D,L-Lactide | 10.0 gm (0.0694 M) | 185° C./4 hrs |  |  |  |
|   | 1,6-hexanediol | 0.656 gm (0.00555 M) | 150° C./1.5 hrs |  |  |  |
|   |  |  | 120° C./3 hrs |  |  |  |

*Determined on a differential scanning calorimeter (TA2100 DSC) using 2–10 mg sample and heating rate of 10° C./min in a nitrogen atmosphere
**In hexofluoroisopropanol Functional interchange of polycarboxylic or hydroxy-polybasic organic acid with preformed high molecular weight polyesters with COOH/OH ratio of unity to virtually zero, preferably in the presence of an organometallic catalyst, e.g. melt-reaction of an 85/15 lactide/glycolide copolymer with a molecular weight greater than 5,000 and COOH/OH≦1 with DL-malic acid in the presence of stannous octoate, to produce the lower molecular weight polyesters with COOH/OH≧1, entails heating a high molecular weight polyester with a predetermined amount of polycarboxylic or hydroxy-polycarboxylic acid in the presence of a trace amount an organometallic catalyst such as stannous octoate. The reactants are heated above 150° C. under dry were determined by HPLC using a Waters Model 6000 solvent delivery pump and a Dynamax (Rainin) model UV-D detector (205 nm, 1.0 AUFS). Runs were performed using 0.025N $Na_2PO_4$ buffer, pH=3.5 (isocratic flow rate= 1.0 ml/min.) using a Nucleosil C18, 5 um, 25 cm×4.6 mm column.

The desired polyester is isolated and purified as described above for ring-opening polymerization. An example of a polyester made by this process and pertinent analytical data are given in Table IV.

TABLE IV

POLYESTERS MADE BY FUNCTIONAL INTERCHANGE

Type IV Polyesters

| Polymer # | Charge | | Polymerization Conditions | Acid # | $\eta$inh | Tg, ° C.* |
|---|---|---|---|---|---|---|
| 1 Boehringer A001 | 8 gm (50/50 di-Lactide/Glycolide) | | 150° C./5 hrs | 670 | 0.26 | 25 |
| Citric Acid | 0.8 gm (0.00417 M) | | | | | |

*Determined on a differential scanning calorimeter (TA2100 DSC) using 2–10 mg sample and heating rate of 10° C./min in a nitrogen atmosphere
**A catalytic amount of stannous octoate (2 drops of 0.33 M solution approximately 0.03 nmole).

Among the other monomers suitable for the synthesis of the polyesters used in the invention are: L-lactic acid, DL-lactic acid, $\epsilon$-caprolactone, p-dioxanone, $\epsilon$-caproic acid, trimethylene carbonate, 1,5-dioxepan-2-one, 1,4-dioxepan-2-one, glycolide, and meso-lactide. Examples of useful polycarboxylic chain initiators and/or chain modifiers include malic acid, citric acid and tartaric acid.

(2) Synthesis of the polyester/polypeptide ionic conjugate by ionic interaction of polycarboxylic acid-tipped polyesters and biologically active polypeptides The polycarboxylic acid-tipped biodegradable polyesters described above are used to make an ionic molecular conjugates with mono- or polycarboxylic oligopeptides, polypeptides or proteins with accessible effective ionogenic amine groups (see FIG. 2). Moreover, any polyester is rendered capable of forming an ionic molecular conjugate with a polypeptide provided it is treated with a base, e.g., 0.1N NaOH. Such treatment exposes acid groups of the polyester for multiple site ionic interaction with the cationic polypeptide.

Thus, the formation of these conjugates is achieved by direct molecular interaction of the components in the proper solvent with or without a pretreatment of the polyester with an inorganic base to maximize its binding rate capacity to the basic drug. As noted above, the ionic interaction of their ionic conjugate components increases within the difference in their pKa values.

The polyester is dissolved in a suitable aprotic solvent in a concentration range of 2% to 20% W/V. Such solvents should dissolve the polyesters, but also be partly miscible with water. Suitable solvents used for this purpose include tetrahydrofuran, acetone, and ethylene glycol dimethylether. To this solution, an aqueous solution of base such as sodium, potassium or ammonium hydroxide or carbonate is added to maximize the binding capacity of the polyester. In general, the amount of base added corresponds to the amount of acid represented by the counter-anion level of the basic peptide to be used.

After briefly mixing the polyester-base combination, an aqueous solution of peptide or peptide salt is added at peptide/polyester loading levels of 2% to 50% W/W (peptide/polyester). This mixture is stirred for a period of time (up to 3 hours), and then the solvents are removed and the product is dried under vacuum. The resulting material may then be further processed for dosage formulation. The resulting pharmaceutical compositions are designed to be chemically uniform compositions made totally of ionic molecular conjugates and are essentially devoid of microscopically or macroscopically dispersed domains of the active drug in the biodegradable matrix. Examples of prepared ionic molecular conjugates and pertinent analytical data are given in Table V.

TABLE V

IONIC MOLECULAR CONJUGATE-PEPTIDE BINDING[1]

| Polymer Used | Peptide[2] | Loading % | Retention[3] % |
|---|---|---|---|
| 1 50/50 dl Lactide/Glycolide | I | 10 | 47 |
| (Commercial) | I | 20 | 25 |
| Acid # = 22,000 | II | 20 | 73 |
| $\eta$inh = 0.53 | III | 20 | 48.5 |
| 2 Poly L-Lactide | I | 10 | 62 |
| (Commercial) | II | 20 | 40 |
| Mw (ave) = 2,000 | | | |
| Acid # = 850 | | | |

TABLE V-continued

IONIC MOLECULAR CONJUGATE-PEPTIDE BINDING[1]

| Polymer Used | Peptide[2] | Loading % | Retention[3] % |
|---|---|---|---|
| 3 Poly L-Lactide | I | 10 | 54 |
| (Commercial) | | | |
| Mw (ave) = 50,000 | | | |
| Acid # = 2100 | | | |
| 4 48/48/4 Poly d,1-Lactide/ | I | 20 | 43 |
| Glycolide/1,6 hexanediol | | | |
| (Method III) | | | |
| Acid # = 10,138 | | | |
| $\eta$inh = 0.39 | | | |
| 5 49/49/2 Poly L-Lactic/ | I | 10 | 100 |
| Glycolic/Malic Acid | I | 20 | 99 |
| (Type IB) | I | 30 | 95.5 |
| Acid # = 1400 | I | 40 | 96.0 |
| $\eta$inh = 0.20 | I | 50 | 99.8 |
| | II | 20 | 99.8 |
| | III | 20 | 77.5 |
| 6 83.3/14.7/2 Poly L-Lactic/ | I | 20 | 96 |
| Glycolic/Citric Acid | | | |
| (Type IA) | | | |
| Acid # = 563 | | | |
| $\eta$inh = 0.24 | | | |
| 7 49/49/2 Poly d,1-Lactide/ | I | 20 | 96 |
| Glycolide/Malic Acid | | | |
| (Type II) | III | 20 | 73.9 |
| Acid # = 1200 | | | |
| $\eta$inh = 0.21 | | | |
| 8 48/48/4 Poly d,1-Lactide/ | I | 10 | 90 |
| Glycolide/Citric Acid | | | |
| (Type III) | | | |
| Acid # = 589 | | | |
| $\eta$inh = 0.22 | | | |

[1]In all cases, conjugates were formed as outlined in text using acetone as solvent and sodium hydroxide as base. All peptides used were in the acetate salt form.
[2]Peptides: I BIM-21003 D-Trp$^6$-LHRH(pGlu-His-Trp-Ser-Tyr-D-Trp-Leu-Arg-Pro-Gly NH$_2$) pka = 10.1

II BIM-23014 (H$_2$N-$\beta$-D-Nal-Cys-Tyr-Trp-Lys-Val-Cys-Thr NH$_2$
pka = 9.8

III BIM-26226 (H$_2$N-D-F$_5$Phe-Gln-Trp-Ala-Val-D-Ala-His-Leu-OCH$_3$)pKa = 8.0
[3]% Retention: Measured by rinsing the dried polyester/peptide ionic conjugates with D.I. water and quantitating soluble peptide in rinses by HPLC $$\% \text{ Retention} = 100\% \times \frac{\text{Wt. Peptide Loaded} - \text{Wt. Soluble Peptide}}{\text{Wt. Peptide Loaded}}$$

(3) Conversion of ionic conjugates to implants, rods, microspheres or microparticles capable of releasing in vivo the therapeutic agent for at least 20 days in a monophasic profile The ionic conjugate salts of the invention can be converted to:

(A) sterile injectable microspheres (with or without 0.1 to 10% of a solid polyhydric alcohol as processing aid) containing 1 to 50% by weight polypeptide that can be released according to an essentially monophasic profile and to sustain pharmacological activity over a period of one to 12 weeks; (B) sterile implantable films made by casting, pressing or extrusion with or without a pharmacologically inactive processing aid, and capable of providing a release profile similar to that described in (A) and; (C) sterile injectable rods made by extrusion or pressing, capable of providing a release profile similar to that described in (A). Further, rods can be coated with a polyester to provide an additional layer of control over the rate of release of a therapeutic agent. Preferably, the rods are coated with an absorbable polyester; more preferably the absorbable polyester is as defined herein and most preferably the coating absorbable polyester is the same as the polyester comprised in the rod.

In-Vitro Release Assay

Samples of the dried and ground ionic conjugate material weighing 50 mg each were placed in 25 mm diameter scintillation vials. A 5 ml aliquot of modified PBS buffer (PBS buffer 2.87 gm $Na_2HPO_4$, 0.654 gm $NaH_2PO_4$, 5.9 gm NaCl, 0.5 gm $NaN_3$, Q.S. 1.0 Liter with Deionized water; pH=7.27.) was added to each vial and the vials were placed in a Lab-Line Orbit Environ-Shaker and swirled at 120 R.P.M. and 37° C. Vials were withdrawn periodically and decanted and replenished with fresh PBS solution. The amount of released peptide was determined from the decanted PBS solutions by HPLC.

Peptide Extraction From Ionic Conjugates

A 50 mg sample of an ionic molecular conjugate was mixed into 20 mls of methylene chloride. The mixture was sequentially extracted with 50 ml, 20 ml and 20 ml portions of 2N acetic acid. The acetic acid extracts were combined and analyzed for peptide content by high performance liquid chromatography (HPLC). Peptide analysis by HPLC is as follows. HPLC analysis were performed using a Waters model M-45 solvent delivery pump and an EM Science MACS 700 detector at wavelength 220 nm and 1.0 AUFS. Peptides were run using a Lichrospher (EM separations) C18, 100Å, 5 μm, 25 cm×4.6 mm column and 30% acetonitrile/0.1% TFA as an isocratic eluent buffer.

Following are details (Table VI) of the in vitro assay demonstrating the amount of peptide released over a 28 day period for 49:49:2 L-Lactic/Glycolic/Malic\D-$Trp^6$[LHRH] (Example #8), 49:49:2:L-Lactic/Glycolic/Malic\Somatostatin-Tumor Inhibiting Analogue (Example #9), and 73.5:24.5:2 poly-L-lactide/glycolic/Malic:D-$Trp^6$[LHRH] (Example #10) ionic molecular conjugates.

TABLE VI

IN-VITRO ASSAY DATA

| DAY OF ASSAY | PERCENT OF TOTAL PEPTIDE RELEASED | | |
|---|---|---|---|
| | Example #8 | Example #9 | Example #10 |
| 1 | 5.5% | 12.5% | 11% |
| 7 | 26.9% | 21.3% | 53% |
| 14 | 55.2% | 47.3% | 55% |
| 17 | 84.4% | 72.2% | 60% |
| 21 | 98.6% | 82.5% | 66% |
| 24 | 100% | 98.2% | 75% |
| 28 | — | 99.6% | — |

Quantitation of Peptides in Ionic Conjugates

Ionically bound peptides in the conjugate products were measured by dissolving 10 mg of sample in 5.7 ml of a 9:1 mixture of acetone and 0.1M aqueous trifluoroacetic acid. The solutions were swirled at about 25° C. for about 15–24 hours and then filtered through 0.5 μm teflon filter cartridges. The filtrates were then analyzed for peptide content by high performance liquid chromatography (HPLC). Peptide analysis by HPLC were run using a Millipore model 717 Wisp Autosampler, a model 510 pump and a model 486 UV detector set at 220 nm. Peptides were run on a Lichrospher (EM Separations) 25 cm×4.6 mm C18, 5 μm 100 Å column, flow rate 1.0 ml per minute using 35% acetonitrile in 0.14% sodium perchlorate buffer as an isocratic eluent system. Peptides were quantified by comparison of the area of the correct peak in the sample run with the area of a injected peptide standard.

Use

Any of the acid-bearing polyesters/polypeptide ionic conjugates described herein can be administered to a recipient alone or in combination with a pharmaceutically-acceptable medium. Although it may be convenient to administer subcutaneously, intramuscularly, parenterally, by suppository or nasally, the therapeutic preparation is administered in accordance with the condition to be treated. The concentration of the composition in the formulations of the invention will vary depending upon a number of issues, including the dosage to be administered, and the route of administration.

Without further elaboration, it is believed that one skilled in the art can, using the preceding description, utilize the instant invention to its fullest extent. The following embodiments are, therefore, to be construed as merely illustrative, and not limitative of the remainder of the disclosure in any way whatsoever.

EXAMPLE 1—DIRECT CONDENSATION METHOD

Synthesis of 50/50 Poly (D,L-Lactic-co-glycolic) Catalyzed by Amerlyst 15

D,L-lactic acid (85% aqueous mixture; 13.7 gm, 0.13 mole) was mixed with glycolic acid (10 gm, 0.13 mole) in a round bottom flask fitted with a magnetic stirrer, a Dean-Stark trap and a water cooled condenser. Toluene (100 ml) and Amberlyst 15 beads (100 mg) were added and the mixture was refluxed under nitrogen for 72 Hours, removing water from the mixture. The mixture was cooled, toluene was decanted from the solidified mass and the product was dissolved in methylene chloride (250 ml). The methylene chloride solution was treated with activated charcoal (Darco, 500 mg), filtered and vacuum dried in a rotary evaporator. The polyester was further dried under high vacuum (1 mm Hg) at 40° C. to afford a white powder. ($_{\eta inh}$ in $CHCl_3$=0.3, Acid #=2439, Tg=12° C.)

EXAMPLE 2—DIRECT CONDENSATION METHOD

Synthesis of 49/49/2 Poly(L-Lactic-co-glycolic/citric) Catalyzed by Amberlyst 15

Using a system similar to above, L-lactic acid (88% aqueous mixture; 25.6 gm, 0.25 mole) was combined with glycolic acid (19.2 gm, 0.25 mole), citric acid monohydrate (2.33 gm, 0.011 mole), Amberlyst 15 beads (500 mg) and toluene (150 ml) in a round bottom flask. The mixture was heated with stirring to reflux for 51 hours, removing water by the Dean-Stark trap. The toluene was decanted from the semi solid product. The polyester was dissolved into acetone (300 ml) and filtered and dried on a rotary evaporator. The solid polyester was then redissolved in methylene chloride and was washed twice with water (2×150 ml) to remove soluble oligomers. The organic solution was concentrated on a rotary evaporator and the product was thoroughly dried under vacuum to afford a white solid (see Table I, Type IB Polyester, Polymer #4). ($_{\eta inh}$ in $CHCl_3$=0.11, Acid #=842, Tg=15° C.)

EXAMPLE 3—STEP GROWTH POLYMERIZATION METHOD

Synthesis of 73.5/24.5/2 Poly(L-Lactide-co-glycolic/malic) Catalyzed by Malic Acid Using a 150 ml capacity cylindrical ampule with an air impinger fitting L-lactide (20 gm, 0.139 mole) was combined with glycolic acid (7.1 gm, 0.093 mole) and (d,l)-malic acid (1.0 gm, 0.0075 mole). The mixture was agitated by bubbling nitrogen through the impinger inlet (100 ml/min) and heated from 25° C. to 155° C. over 100 minutes. The reaction temperature was maintained at 155° C. for 70 hours and the water from polymerization was removed in a cold trap on the reactor outlet line. After 70 hours the reaction was cooled to 100° C. and poured into a chilled stainless steel receiver for hardening. The solid polyester was then dissolved in methylene chloride and was washed twice with water (2×150 ml) to remove soluble oligomers. The organic solution was concentrated on a rotary evaporator and the product was thoroughly dried under vacuum to afford a white solid (see Table II, Type II Polyester, Polymer #2). ($_\eta$inh in $CHCl_3$=0.13, Acid #=1800, Tg=27° C.)

EXAMPLE 4—RING OPENING POLYMERIZATION METHOD

Synthesis of 75/25 Poly(L-lactide-co-glycolide) Initiated by Malic Acid

L-lactide (12.0 g, 0.0833 mole), glycolide (3.21 g, 0.0277 mole), malic acid 0.3042 g, 0.00227 mole), and stannous octoate catalyst (0.33 M in toluene, 67 μL, 0.022 mmole) were added under dry nitrogen conditions to a glass ampule with a magnetic stirrer. The system was purged with $N_2$ and evacuated with vacuum several times before sealing the ampule. The reactants were then melted at 140° C. and the melt was heated at 180°, 190°, 180°, and 150° for 1, 4.5, 12, and 2 hours, respectively. After cooling to room temperature, the polyester was reheated to 110° C. under a vacuum of less than 1 mm Hg for about one hour to remove monomer, recooled at room temperature, quenched in liquid nitrogen, isolated and dried under vacuum. ($_{\eta inh}$in $CHCl_3$=0.20, Acid #=2560, $T_g$=39° C.)

EXAMPLE 5—RING OPENING POLYMERIZATION METHOD

Synthesis of 50/50 Poly(D,L-lactide-co-glycolide) Initiated by Citric Acid

D,L-lactide (10.0 g, 0.0694 mole) was mixed with glycolide (8.06 g, 0.0694 mole), citric acid (1.07 g, 0.00555 mole) and stannous octoate catalyst (0.33 M in toluene, 84 μL, 0.0278 mmole) under a dry nitrogen atmosphere in a glass ampule containing a magnetic stirrer and sealed under vacuum. The reactants were melted and heated at 180°, 185°, 195°, and 120° C. for 1, 2, 7, and 9 hours, respectively. The polyester was cooled to room temperature, quenched in liquid nitrogen, isolated, and dried. ($_{\eta inh}$in $CHCl_3$=0.26, Acid #=970, $T_g$=23° C.)

EXAMPLE 6—RING OPENING POLYMERIZATION METHOD

Synthesis of 50/50 Poly(D,L-lactide-co-glycolide) Initiated by 1,6-hexanediol

Using a system similar to those described above, D,L-lactide (10.0 g, 0.0694 mole), glycolide (8.06 g, 0.0694 mole), 1,6-hexanediol (0.656 g, 0.00555 mole), and stannous octoate (0.33 M in toluene, 84 μL, 0.0278 mmole) were added under dry nitrogen conditions to a glass ampule which was subsequently sealed under vacuum. The constituents were heated at 150°, 185°, 150°, and 120° C. for 0.5, 4, 1, 5, and 3 hours, respectfully. The resulting polyester was recovered and dried (see Table III, Type III Polyester, Polymer #5). ($_{\eta inh}$in $CHCl_3$=0.39, Acid #=10,138, $T_g$=30° C.)

EXAMPLE 7—FUNCTIONAL INTERCHANGE METHOD

Synthesis of Carboxylic-Bearing 50/50 Poly(D,L-lactide-co-glycolide)

50/50 poly(D,L-lactide-co-glycolide) (Boehringer A001, 8 g), citric acid (0.8 g, 4.16 mmole), and stannous octoate (2 drops) were added to a glass ampule under dry nitrogen conditions and sealed. The mixture was heated at 150° for 4 hours, cooled to room temperature, quenched in liquid nitrogen, isolated, and dried (see Table IV, Type IV Polyester, Polymer #1). ($_{\eta inh}$in $CHCl_3$=0.26, Acid #=670, $T_g$=23° C.)

EXAMPLE 8

Synthesis of a 49:49:2 L-Lactic/Glycolic/Malic (See Table I, Polymer #4) and D-Trp$^6$ [LHRH] Ionic Molecular Conjugate 500 mg of 49:49:2 L-Lactic/Glycolic/Malic (synthesized by direct condensation; Mw=9,500; Acid#=1420) was dissolved in 10 mls of Acetone (Mallinckrodt Analytic Reagent). A portion of 0.1N sodium hydroxide solution (1.14 ml) was added and the mixture was stirred at room temperature for 15 minutes. A solution of 100 mg of D-Trp$^6$ [LHRH] (BIM-21003 Peptide I; base content 87%, acetate content 7%) in 1.0 ml water was added and the mixture was stirred for 1 hour at room temperature. The solvents were then removed, first by Rotovap at T<40° C. and then in a desiccator for 1 hour at room temperature under 1 mm Hg vacuum. The dried solid was triturated and stirred in 100 mls of deionized Water and isolated by filtration. The aqueous filtrate was tested by HPLC and found to contain <1 mg soluble peptide. The solid material was dried several days in vacuo to give 540 mg of white powder. The powder was used in an in vitro assay (see Table VI, Example #8).

EXAMPLE 9

Synthesis of a 49:49:2 L-Lactic/Glycolic/Malic, See Table I, Polymer #4) and Somatostatin/Tumor Inhibiting Analogue Ionic Molecular Conjugate 100 mg of 49:49:2 L-Lactic/Glycolic/Malic (synthesized by direct condensation; Mw=9,500; Acid #=1420) was dissolved in 2 mls of acetone (Mallinckrodt Analytic Reagent). A portion of 0.1N sodium hydroxide solution (0.32 ml) was added and the mixture was stirred at room temperature for 15 minutes. A solution of 20 mg of Somatostatin/Tumor Inhibiting Analogue (BIM-23014 Peptide II; base content 83%, acetate content 9.8%) in 1.2 ml water was added and the mixture was stirred for 1 hour at room temperature. The solvents were then removed, first by Rotovap at T<40° C. and then in a desiccator for 1 hour at room temperature under 1 mm Hg vacuum. The dried solid was triturated and stirred in 20 mls of Deionized Water and isolated by filtration. The aqueous filtrate was tested by HPLC and found to contain <0.05 mg soluble peptide. The solid material was dried several days in vacuo to give 106 mg of white powder. The powder was ground and used in an in vitro release assay (see Table VI, Example #9).

EXAMPLE 10

Synthesis of a 73.5:24.5:2 Poly L-Lactide/Glycolic/Malic (See Table II, See Polymer #2) and D-Trp$^6$ [LHRH] Ionic Molecular Conjugate 800 mg of 73.5:24.5:2 poly L-lactide/glycolic/malic (synthesized by step growth of acyclized products; Acid#=

1800) was dissolved in acetone (16 ml). A portion of 0.1N sodium hydroxide solution (2.8 ml) was added and the solution was stirred at room temperature for 20 minutes. A solution of 200 mg of D-Trp[6] [LHRH] (BIM-21003; base content 87%, acetate content 7%) in 2 ml water was added and the mixture was stirred for 90 minutes. The solvents were removed and the resulting solid was triturated in deionized water as in Example 8 indicating less than 1% soluble peptide salt present. The isolated solids were dried 4 days in vacuo to give 839 mg of white powder. The powder was ground and used for in vitro release assay (see Table VI, Example #10).

EXAMPLE 11

Formation of Peptide-Polymer Ionic Conjugate Microparticle 1.50 of L-Lactide/Glycolide/d,l Malic Acid Polyester (65:33:2)

Conjugates were synthesized by ring opening polymerization as in example 4 (MW=4700 polydispersity=1.3 as determined by GPC on a Jordi Gel 50×1 cm mixed linear bed column, THF eluent, Wyatt Mini Dawn light scattering detector dn/dc=0.05, acid # 1475 by titration, $T_g$=42° C.), was dissolved in 40 ml of acetone. The acid groups were neutralized with 2.0 ml of 0.5M sodium hydroxide solution and stirred for 5 minutes. A solution of 0.5 g of BIM-23014 (peptide content 83.7%, acetate content 11.5%) in 20 ml of Milli-Q water was slowly added with mixing to the polymer solution. An additional 40 ml of acetone was also added portionwise during the peptide addition to prevent precipitation. The clear, colorless solution was stirred for one hour and then evaporated to dryness under vacuum. The resulting white solid was redissolved in a mixture of 20 ml of acetone and 2 ml of Milli-Q water to form a clear solution. This solution was injected, via a 0.2μ teflon filter into a rapidly stirring reservoir of 500 ml Milli-Q water at 4° C. The polymer/peptide complex phase separated immediately into small particles upon contact with the water. After mixing the slurry for 30 min at 4° C., the residual acetone was removed under reduced pressure and the solids were isolated by centrifugation, resuspended with 100 ml of Milli-Q water, and recentrifuged. The isolated solids were dried by lyophilization to give 1530 mg of white free flowing powders. Particle size range=2–100 μm. The $T_g$ of the ionic conjugate was shown to occur at 53° C. Total residual (unbound) peptide in all aqueous supernatants was found to be 63 mg by HPLC analysis. The total initial peptide content was determined by elemental nitrogen analysis to be 19.9% by weight. The percentage of extractable peptide from the conjugate was determined to be 16.9%, by weight, using the acetone/0.1M TFA extraction technique. The resulting conjugate, thus, retains 84.8% ionic (extractable) character.

ROD DELIVERY SYSTEM TYPE 1 (CONC2 AND CGC1)

EXAMPLE A-1

Preparation of Citric Acid Initiated 97/3 Caprolactone/Glycolide Copolymer (CGC1)

A round bottom flask equipped for mechanical stirring was flame dried twice and purged with dry argon. The flask was charged with ϵ-caprolactone (1.455 moles, 166 g), glycolide (0.08865 moles, 10.3 g), citric acid (0.075 moles, 14.4 g), and stannous octoate (0.0003 moles, 375 :l of 0.8 M solution in toluene). The polymerization was conducted using the following scheme: Under argon purge the charge was heated from room temperature to about 150° C. over a period of about 1 hour and about 20 minutes with continuous stirring after melting (at 70 rpm). The charge was maintained at about 150° C. for about 11.5 hours. At the conclusion of the polymerization, the small amount of unreacted monomer was distilled at about 120° C. for about 15 minutes under vacuum (about 0.1 mm Hg). The material was poured into jars and allowed to cool.

The polymer was analyzed by GPC (Mn=3543, Mw=7708), FTIR, DSC (Tm 52.0° C.), and titration for carboxylic content (average equivalent weight=623 Da).

Twenty grams of polymer were dissolved in 50.0 mL acetone, and solution was precipitated in stirring ice-water. The solid product was isolated by filtration.

The purified polymer was analyzed by GPC (Mn=4214, Mw=9688), DSC (Tm 45.2° C.), and titration (average equivalent weight=780).

EXAMPLE B-1

Preparation of Ionic Conjugate (CONC1)

A 1.5 g purified polymer (CGC1) was dissolved in 7.5 mL acetonitrile in a glass vial. In a separate vial 250.0 mg LHRH-acetate was dissolved in 1.5 ml distilled water. The dissolved polymer was filtered through a 0.45 μm Acrodisc syringe filter into a vial containing 83.8 mg sodium carbonate (to neutralize LHRH acetate). The LHRH solution was added dropwise to the filtered polymer solution. The combined solution was mixed with a magnetic stir bar for about 1.5 hours at room temperature. Conjugate was precipitated by adding it dropwise into stirring liquid-nitrogen cooled isopropyl alcohol (IPA). The precipitate was collected by centrifugation and dried over night under vacuum. The conjugate yield was 73.5%. Conjugate was analyzed by DSC (Tm 50.9° C.) and FTIR. Elemental analysis of the material yielded 1.81% nitrogen. Based upon this, the LHRH content was determined to be 10.0%.

EXAMPLE C-1

Preparation of a Rod Form Delivery System

Ionic conjugate (0.3987 g of CONC2) and polymer (1.206 g of CGC1) were mixed by gentle grinding and melted together at about 58° C. in a heating block. The melted material was mixed and then drawn into 18 G capillary tubes and allowed to cool. It was extruded and the rods cut into lengths that had the proper dosage of drug and placed into a sterile 10-gauge spiral needle (ready for injection). All steps of Example C-1 were conducted in a laminar flow hood. The rods had a LHRH content of 2.5%.

ROD DELIVERY SYSTEM TYPE 2 (CONC2 AND CGC1)

EXAMPLE A-2

Preparation of Citric Acid Initiated 97/3 Caprolactone/Glycolide Copolymer (CGC1)

The same polymer (CGC1) made in Example A-1 was used in this example.

EXAMPLE B-2

Preparation of Ionic Conjugates (CONC2)

CONC2 was prepared according to the procedure described in Example B-1. By elemental analysis, the percent nitrogen was 2.31%. Based on this the LHRH content was 12.76%.

EXAMPLE C-2

Preparation of a Rod Form Delivery System

CONC2 (0.1854 g) and 0.5565 g of purified CGC1 were mixed mechanically and then heated to about 60° C. Mixed and melted material was drawn up into 18-gauge capillary tubes and extruded with a plunger. The rods were cut into lengths that had the proper dosage of drug and placed into a sterile 18-gauge spinal needle (ready for injection). All steps of Example C-2 were conducted in a laminar flow hood. The rods had a LHRH content of 3.2%.

ROD DELIVERY SYSTEM TYPE 3

EXAMPLE A-3

Preparation of Tartaric Acid Initiated 98/2 Caprolactone/Trimethylene Carbonate (TMC) Copolymer (CTT1)

A round bottom flask equipped for mechanical stirring was flame dried three times and purged with dry argon. The flask was charged with $\epsilon$-caprolactone (1.47 moles, 168 g), TMC (0.03 moles, 3.06 g), tartaric acid (0.0142 moles, 2.134 g), and stannous octoate (0.0003 moles, 375 :1 of 0.8 M solution in toluene). The polymerization was conducted using the following scheme: Under argon purge the charge was heated from room temperature to about 150° C. over a period of about 1 hour while stirring the molten reaction mixture (60 rpm). The temperature was maintained at about 150° C. for about 9 hours. Unreacted monomer was distilled at about 100° C. for about 1 hour under reduced pressure (0.1 mm). The polymer was poured into jars and allowed to cool.

Polymer was analyzed by GPC (Mn=13221, Mw=35602).

EXAMPLE B-3

Preparation of Ionic Conjugates (CONCTT1)

A 1.5 g purified polymer from Example A-3 was dissolved in 7.5 mL acetonitrile in a glass vial. In a separate vial, 250 mg LHRH-acetate was dissolved in 1.5 ml distilled water. The dissolved polymer was filtered through a 0.45 $\mu$m Acrodisc syringe filter into a vial containing 56.5 mg sodium carbonate (to neutralize LHRH-acetate). The LHRH solution was added dropwise to the filtered polymer solution. The combined solution was mixed with a magnetic stir bar for about 3 hours at room temperature. Conjugate was precipitated by adding it dropwise into stirring liquid nitrogen cooled IPA. The precipitate was collected by centrifugation and dried over night under vacuum.

The conjugate yield was 81.1%. Elemental analysis of the material yielded 2.04% nitrogen. Based upon this, the LHRH content was determined to be 11.3%.

EXAMPLE C-3

Preparation of a Rod Form Delivery System

CTT1 (0.8909 g) was melted at about 55° C. To this was added 0.2250 g of CONCTT1 and the entire system was heated to about 65° C. The molten system was then drawn up into 18 gauge capillary tubes and extruded with a plunger. The rods were cut into lengths that had the proper dosage of drug and placed into a sterile 18 gauge spiral needle (ready for injections). All steps of example C-3 were conducted in a laminar flow hood. The rods had an LHRH content of 2.3%.

ROD DELIVERY SYSTEM TYPE 4

EXAMPLE A-4

Preparation of Tartaric Acid Initiated 94/6 Caprolactone/Glycolide Copolymer (CGT6)

A round bottom flask equipped for mechanical stirring was flame dried three times and purged with dry argon. The flask was charged with $\epsilon$-caprolactone (1.41 moles, 161 g), glycolide (0.09 moles, 10.4 g), tartaric acid (0.005 moles, 0.73 g), and stannous octoate (0.0003 moles, 375 :1 of 0.8 M solution in toluene). The polymerization was conducted using the following scheme: Under argon purge the charge was heated from room temperature to about 150° C. over a period of about 1 hour while stirring the molten reaction mixture (60 rpm). The temperature was maintained at about 150° C. for about 1 hour. It was then raised to about 180° C. for about four hours. Material was cooled to about 107° C. and placed under vacuum at 1.5 mm Hg for about 1.5 hours. The material was poured into jars and allowed to cool.

After collection, the polymer was analyzed by DSC (Tm=54.5 C) and GPC (Mn=26254 Mw=68101).

EXAMPLE B-4

Preparation of Ionic Conjugates (CONCTT2)

CONCTT2 was prepared as described in Example B-1 but using LHRH-acetate and the copolymer of Example A4.

EXAMPLE C-4

Preparation of a Rod Form Delivery System

CGT6 (1.4 g) and CONCTT2 (0.4779 g) were heated to about 57° C., cooled, chopped, then reheated to the same temperature. The molten system was then drawn up into 18 gauge capillary tubes and extruded with a plunger. The rods were cut into lengths that had the proper dosage of drug and placed into a sterile 18 gauge spiral needle (ready for injections). All steps of Example C-4 were conducted in a laminar flow hood. The rods had an LHRH content of 2.8%.

EXAMPLE D-4

Coating of System C-4 Rod Using Inert Copolymer Precursor

CGT6 (1.4 g) was dissolved in 1.5 ml dichloromethane. The rods from Example C-4 were dipped into this polymer solution, immediately removed, and dried under ambient conditions in a laminar flow hood.

From the foregoing description, one skilled in the art can easily ascertain the essential characteristics of this invention, and without departing from the spirit and scope thereof, can make various changes and modifications of the invention to adapt it to various usages and conditions. Thus, other embodiments are also within the claims.

What is claimed is:

1. A polyester containing one or more free COOH groups and having a carboxyl to hydroxyl ratio greater than one, wherein said polyester contains a member selected from the group consisting of L-lactic acid, D-lactic acid, DL-lactic acid, malic acid, citric acid, $\epsilon$-caprolactone, p-dioxanone, $\epsilon$-caproic acid, alkylene oxalate, cycloalkylene oxalate, alkylene succinate, β-hydroxybutyrate, substituted or unsubstituted trimethylene carbonate, 1,5-dioxepan-2-one, 1,4-dioxepan-2-one, glycolide, glycolic acid, L-lactide, D-lactide, DL-lactide, meso-lactide, and any optically active isomers, racemates or copolymers thereof, provided that citric acid, $\epsilon$-caprolactone and glycolide are members of the polyester.

2. A polyester according to claim 1, wherein the polyester comprises citric acid, $\epsilon$-caprolactone and glycolide.

3. A polyester according to claim 2, wherein the ratio of $\epsilon$-caprolactone to glycolide in the polyester is from 90 $\epsilon$-caprolactone:10 glycolide to 99 $\epsilon$-caprolactone:1 glycolide.

4. A polyester according to claim 3, wherein the ratio of $\epsilon$-caprolactone to glycolide in the polyester is 97 $\epsilon$-caprolactone:3 glycolide.

5. A composition comprising a polyester according to claim 1 ionically conjugated to one or more bioactive polypeptide comprising at least one effective ionogenic amine, wherein at least 50%, by weight, of the polypeptide present in the composition is ionically conjugated to the polyester.

6. A composition comprising a polyester according to claim 2 ionically conjugated to one or more bioactive polypeptide comprising at least one effective ionogenic amine, wherein at least 50%, by weight, of the polypeptide present in the composition is ionically conjugated to the polyester.

7. A composition comprising a polyester according to claim 3 ionically conjugated to one or more bioactive polypeptide comprising at least one effective ionogenic amine, wherein at least 50%, by weight, of the polypeptide present in the composition is ionically conjugated to the polyester.

8. A composition comprising a polyester according to claim 4 ionically conjugated to one or more bioactive polypeptide comprising at least one effective ionogenic amine, wherein at least 50%, by weight, of the polypeptide present in the composition is ionically conjugated to the polyester.

9. A polyester containing one or more free COOH groups and having a carboxyl to hydroxyl ratio greater than one, wherein said polyester contains a member selected from the group consisting of L-lactic acid, D-lactic acid, DL-lactic acid, malic acid, citric acid, tartaric acid, $\epsilon$-caprolactone, p-dioxanone, $\epsilon$-caproic acid, alkylene oxalate, cycloalkylene oxalate, alkylene succinate, β-hydroxybutyrate, substituted or unsubstituted trimethylene carbonate, 1,5-dioxepan-2-one, 1,4-dioxepan-2-one, glycolide, glycolic acid, L-lactide, D-lactide, DL-lactide, meso-lactide, and any optically active isomers, racemates or copolymers thereof, provided that tartaric acid is a member of the polyester.

10. A polyester according to claim 9, wherein the polyester comprises L-lactic acid or D-lactic acid; or wherein the polyester comprises L-lactic acid or D-lactic acid and glycolic acid.

11. A polyester according to claim 9, wherein the polyester comprises tartaric acid, $\epsilon$-caprolactone and trimethylene carbonate.

12. A polyester according to claim 11, wherein the ratio of $\epsilon$-caprolactone to trimethylene carbonate in the polyester is from 90 $\epsilon$-caprolactone:10 trimethylene carbonate to 99 $\epsilon$-caprolactone:1 trimethylene carbonate.

13. A polyester according to claim 12, wherein the ratio of $\epsilon$-caprolactone to trimethylene carbonate in the polyester is 98 $\epsilon$-caprolactone:2 trimethylene carbonate.

14. A composition comprising a polyester according to claim 9 ionically conjugated to one or more bioactive polypeptide comprising at least one effective ionogenic amine, wherein at least 50%, by weight, of the polypeptide present in the composition is ionically conjugated to the polyester.

15. A composition comprising a polyester according to claim 11 ionically conjugated to one or more bioactive polypeptide comprising at least one effective ionogenic amine, wherein at least 50%, by weight, of the polypeptide present in the composition is ionically conjugated to the polyester.

16. A composition comprising a polyester according to claim 12 ionically conjugated to one or more bioactive polypeptide comprising at least one effective ionogenic amine, wherein at least 50%, by weight, of the polypeptide present in the composition is ionically conjugated to the polyester.

17. A composition comprising a polyester according to claim 13 ionically conjugated to one or more bioactive polypeptide comprising at least one effective ionogenic amine, wherein at least 50%, by weight, of the polypeptide present in the composition is ionically conjugated to the polyester.

18. A composition comprising a polyester according to claim 10 ionically conjugated to one or more bioactive polypeptide comprising at least one effective ionogenic amine, wherein at least 50%, by weight, of the polypeptide present in the composition is ionically conjugated to the polyester.

19. A composition according to claim 5, wherein the bioactive polypeptide is selected from the group consisting of LHRH, somatostatin, bombesin/GRP, calcitonin, bradykinin, galanin, MSH, GRF, amylin, tachykinins, secretin, PTH, CGRP, neuromedins, PTHrP, glucagon, neurotensin, ACTH, GHRP, GLP, VIP, PACAP, enkephalin, PYY, motilin, substance P, NPY, TSH, and analogs or fragments thereof.

20. A composition according to claim 14, wherein the bioactive polypeptide is selected from the group consisting of LHRH, somatostatin, bombesin/GRP, calcitonin, bradykinin, galanin, MSH, GRF, amylin, tachykinins, secretin, PTH, CGRP, neuromedins, PTHrP, glucagon, neurotensin, ACTH, GHRP, GLP, VIP, PACAP, enkephalin, PYY, motilin, substance P, NPY, TSH, and analogs or fragments thereof.

21. A composition according to claim 18, wherein the bioactive polypeptide is selected from the group consisting of LHRH, somatostatin, bombesin/GRP, calcitonin, bradykinin, galanin, MSH, GRF, amylin, tachykinins, secretin, PTH, CGRP, neuromedins, PTHrP, glucagon, neurotensin, ACTH, GHRP, GLP, VIP, PACAP, enkephalin, PYY, motilin, substance P, NPY, TSH, and analogs or fragments thereof.

22. A composition according to claim 19, wherein the bioactive polypeptide is selected from the group consisting of LHRH, somatostatin and analogs or fragments thereof.

23. A composition according to claim 20, wherein the bioactive polypeptide is selected from the group consisting of LHRH, somatostatin and analogs or fragments thereof.

24. A composition according to claim 21, wherein the bioactive polypeptide is selected from the group consisting of LHRH, somatostatin and analogs or fragments thereof.

25. A composition according to claim 22, wherein the LHRH analogue is of the formula pGlu-His-Trp-Ser-Tyr-Trp-Leu-Arg-Pro-Gly-NH$_2$ and the somatostatin analogue is of the formula H$_2$N-β-D-Nal-Cys-Tyr-Trp-Lys-Val-Cys-Thr-NH$_2$, wherein the two Cys residues of the somatostatin analogue are bonded to each other.

26. A composition according to claim 23, wherein the LHRH analogue is of the formula pGlu-His-Trp-Ser-Tyr-D-Trp-Leu-Arg-Pro-Gly-NH$_2$ and the somatostatin analogue is of the formula H$_2$N-β-Nal-Cys-Tyr-Trp-Lys-Val-Cys-Thr- NH$_2$, wherein the two Cys residues of the somatostatin analogue are bonded to each other.

27. A composition according to claim 24, wherein the LHRH analogue is of the formula pGlu-His-Trp-Ser-Tyr-D-Trp-Leu-Arg-Pro-Gly-NH$_2$ and the somatostatin analogue is of the formula H$_2$N-β-D-Nal-Cys-Tyr-Trp-Lys-Val-Cys-Thr-NH$_2$, wherein the two Cys residues of the somatostatin analogue are bonded to each other.

28. A composition according to claim 19, wherein said composition is in the form of a rod.

29. A composition according to claim 20, wherein said composition is in the form of a rod.

30. A composition according to claim 21, wherein said composition is in the form of a rod.

31. A composition according to claim 28, wherein said rod has a coating of a polyester.

32. A composition according to claim 31, wherein the polyester coating the rod is an absorbable polyester.

33. A composition according to claim 32, wherein the absorbable polyester contains one or more free COOH groups and having a carboxyl to hydroxyl ratio greater than one, wherein said polyester contains a member selected from the group consisting of L-lactic acid, D-lactic acid, DL-lactic acid, malic acid, citric acid, tartaric acid, $_\epsilon$-caprolactone, p-dioxanone, $_\epsilon$-caproic acid, alkylene oxalate, cycloalkylene oxalate, alkylene succinate, β-hydroxybutyrate, substituted or unsubstituted trimethylene carbonate, 1,5-dioxepan-2-one, 1,4-dioxepan-2-one, glycolide, glycolic acid, L-lactide, D-lactide, DL-lactide, meso-lactide, and any optically active isomers, racemates or copolymers thereof.

34. A composition according to claim 33, wherein the absorbable polyester coating the rod is the same as the polyester comprised in the composition.

35. A composition according to claim 29, wherein said rod has a coating of a polyester.

36. A composition according to claim 35, wherein the polyester coating the rod is an absorbable polyester.

37. A composition according to claim 36, wherein the absorbable polyester contains one or more free COOH groups and having a carboxyl to hydroxyl ratio greater than one, wherein said polyester contains a member selected from the group consisting of L-lactic acid, D-lactic acid, DL-lactic acid, malic acid, citric acid, tartaric acid, $_\epsilon$-caprolactone, p-dioxanone, $_\epsilon$-caproic acid, alkylene oxalate, cycloalkylene oxalate, alkylene succinate, β-hydroxybutyrate, substituted or unsubstituted trimethylene carbonate, 1,5-dioxepan-2-one, 1,4-dioxepan-2-one, glycolide, glycolic acid, L-lactide, D-lactide, DL-lactide, meso-lactide, and any optically active isomers, racemates or copolymers thereof.

38. A composition according to claim 37, wherein the absorbable polyester coating the rod is the same as the polyester comprised in the composition.

39. A composition according to claim 30, wherein said rod has a coating of a polyester.

40. A composition according to claim 39, wherein the polyester coating the rod is an absorbable polyester.

41. A composition according to claim 40, wherein the absorbable polyester contains one or more free COOH groups and having a carboxyl to hydroxyl ratio greater than one, wherein said polyester contains a member selected from the group consisting of L-lactic acid, D-lactic acid, DL-lactic acid, malic acid, citric acid, tartaric acid, $_\epsilon$-caprolactone, p-dioxanone, $_\epsilon$-caproic acid, alkylene oxalate, cycloalkylene oxalate, alkylene succinate, β-hydroxybutyrate, substituted or unsubstituted trimethylene carbonate, 1,5-dioxepan-2-one, 1,4-dioxepan-2-one, glycolide, glycolic acid, L-lactide, D-lactide, DL-lactide, meso-lactide, and any optically active isomers, racemates or copolymers thereof.

42. A composition according to claim 41, wherein the absorbable polyester coating the rod is the same as the polyester comprised in the composition.

* * * * *

UNITED STATES PATENT AND TRADEMARK OFFICE
CERTIFICATE OF CORRECTION

PATENT NO.    : 6,221,958 B1
DATED         : April 24, 2001
INVENTOR(S)   : Shalaby Wahba Shalaby, Steven A. Jackson and Jacques-Pierre Moreau It is certified that error appears in the above-identified patent and that said Letters Patent is hereby corrected as shown below:

Column 6,
Line 12, that portion of the formula reading "-Tyr-Trp-" should read -- Tyr-D-Trp --

Column 24,
Line 60, that portion of the formula reading "-Trp-" should read -- D-Trp- --

Signed and Sealed this

Fifteenth Day of February, 2005

JON W. DUDAS
*Director of the United States Patent and Trademark Office*